US011464526B2

(12) United States Patent
Aebi et al.

(10) Patent No.: US 11,464,526 B2
(45) Date of Patent: Oct. 11, 2022

(54) SELF-ORIENTING DRILL SLEEVE

(71) Applicant: Depuy Synthes Products, Inc., Raynham, MA (US)

(72) Inventors: This Aebi, Grenchen (CH); Mirko Rocci, Bettlach (CH); Steffan Daniel, Solothurn (CH); Joel Oberli, Niederdorf (CH); Johanna Menze, Zurich (CH); Andreas Baeriswyl, Buren an der Aare (CH); Said Ghammar, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 27 days.

(21) Appl. No.: 17/150,903

(22) Filed: Jan. 15, 2021

(65) Prior Publication Data

US 2022/0226004 A1    Jul. 21, 2022

(51) Int. Cl.
*A61B 17/17* (2006.01)
*A61B 17/16* (2006.01)
*A61B 17/00* (2006.01)

(52) U.S. Cl.
CPC ...... *A61B 17/1728* (2013.01); *A61B 17/1622* (2013.01); *A61B 17/1633* (2013.01); *A61B 2017/00367* (2013.01)

(58) Field of Classification Search
CPC . A61B 17/1633; A61B 17/17; A61B 17/1703; A61B 17/1725; A61B 17/1728; A61B 17/1732
See application file for complete search history.

(56) References Cited

U.S. PATENT DOCUMENTS

| | | | | |
|---|---|---|---|---|
| 5,851,207 A * | 12/1998 | Cesarone | ............ | A61B 17/1728 606/284 |
| 7,357,804 B2 * | 4/2008 | Binder, Jr. | ......... | A61B 17/1728 606/96 |
| 7,887,540 B2 * | 2/2011 | Hontzsch | ............ | A61B 17/1735 606/86 R |
| 8,162,950 B2 * | 4/2012 | Digeser | .............. | A61B 17/1728 606/96 |
| 8,343,195 B2 * | 1/2013 | Rathbun | ............ | A61B 17/1728 606/104 |

(Continued)

OTHER PUBLICATIONS

International Search Report and Written Opinion for PCT/IB2022/050188 dated Apr. 8, 2022.

*Primary Examiner* — Eric S Gibson
(74) *Attorney, Agent, or Firm* — Kramer & Amado, P.C.

(57) ABSTRACT

A drill sleeve, including: an outer sleeve with an internal collet at a distal end of the outer sleeve and an inner opening; a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger wherein the biasing force drives the inner sleeve into the outer sleeve, wherein when a distal end of the inner sleeve engages the internal collet, the internal collet is configured to engage a screw hole in a bone plate, align the drill sleeve with a nominal axis of the screw hole, and secure the drill sleeve to the screw hole.

20 Claims, 11 Drawing Sheets

(56) References Cited

U.S. PATENT DOCUMENTS

| | | | |
|---|---|---|---|
| 8,523,862 B2* | 9/2013 | Murashko, Jr. | A61B 17/1728 606/71 |
| 8,641,743 B2* | 2/2014 | Michelson | A61B 17/8042 606/280 |
| 9,107,678 B2* | 8/2015 | Murner | A61B 17/8057 |
| 9,750,512 B2* | 9/2017 | Jerke | A61B 17/1728 |
| 10,238,439 B2* | 3/2019 | Prybis | A61B 17/80 |
| 11,141,172 B2* | 10/2021 | Laird, Jr. | A61B 17/1728 |
| 2005/0038444 A1* | 2/2005 | Binder, Jr. | A61B 17/1728 606/96 |
| 2005/0137606 A1* | 6/2005 | Binder, Jr. | A61B 17/1728 606/96 |
| 2012/0253347 A1* | 10/2012 | Murashko, Jr. | A61B 17/1782 606/71 |
| 2015/0119943 A1* | 4/2015 | Milella, Jr. | A61B 17/1728 606/280 |
| 2019/0314042 A1 | 10/2019 | Laird, Jr. et al. | |
| 2021/0177471 A1* | 6/2021 | Detweiler | A61B 17/865 |

\* cited by examiner

SELF-ORIENTING DRILL SLEEVE

TECHNICAL FIELD

Various exemplary embodiments disclosed herein relate generally to a self-orienting drill sleeve.

BACKGROUND

In the majority of cases, surgeons prefer to place screws in a nominal plate hole direction. This helps avoiding screw collisions, ensures the best plate-screw connection strength and is designed to fit most of the patients. However finding the nominal screw direction of an orthopedic plate hole is often challenging. Especially in anatomic plates and holes not perpendicular to plate surface. Testing using threaded sleeves in different kind of threaded holes showed mean deviations of up to 5.65° and worst case of 19.5° vs nominal axis. In some types of plate holes there are no other structures than the thread including chamfers which may be used for orientation and fixation of a drill sleeve.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a drill sleeve, including: an outer sleeve with an internal collet at a distal end of the outer sleeve and an inner opening; a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger wherein the biasing force drives the inner sleeve into the outer sleeve, wherein when a distal end of the inner sleeve engages the internal collet, the internal collet is configured to engage a screw hole in a bone plate, align the drill sleeve with a nominal axis of the screw hole, and secure the drill sleeve to the screw hole.

Various embodiments are described, wherein the internal collet includes a plurality of blades configured engage the screw hole.

Various embodiments are described, wherein the internal collet further includes a stop and a locking ridge.

Various embodiments are described, wherein the stop is configured to engage a seat in the screw hole and the locking ridge is configured to engage a locking edge in the screw hole.

Various embodiments are described, wherein a diameter of the internal collet at the locking ridge is less than a smallest diameter of the screw hole.

Various embodiments are described, wherein the biasing member is a leaf spring attached to the handle, wherein the leaf spring includes an engagement member configured to engage a trigger groove on the trigger.

Various embodiments are described, wherein the engagement member is V-shaped.

Various embodiments are described, wherein the distal end if the inner sleeve is substantially cylindrical.

Various embodiments are described, wherein the distal end of the inner sleeve is tapered.

Various embodiments are described, wherein an inner opening of the internal collet is substantially cylindrical.

Various embodiments are described, wherein the inner opening of the internal collet is tapered.

Various embodiments are described, wherein the biasing member is a coil spring surrounding the outer tube and located between the handle and the trigger.

Various embodiments are described, further including a connection member connected to trigger and the inner tube, wherein the connection member passes through a slot in the outer sleeve.

Various embodiments are described, wherein the connection member is a pin that engages a hole in the trigger and a groove in the inner tube.

Further various embodiments relate to a method of drilling a hole in a bone for a bone plate using a drill sleeve, wherein, the drill sleeve, comprises: an outer sleeve with an internal collet at a distal end of the outer sleeve and an inner opening, a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger wherein the biasing force drives the inner sleeve into the outer sleeve, the method including: depressing the trigger of the drill sleeve; inserting the distal end of the outer sleeve into a screw hole of the bone plate; releasing the trigger of the drill sleeve to securely engage the screw hole; drilling a hole in the bone through the screw hole using the drill sleeve; depressing the trigger; and removing the distal end of the outer sleeve from the screw hole.

Various embodiments are described, wherein securely engaging the screw hole includes aligning the drill sleeve with a nominal direction of the screw hole.

Further various embodiments relate to a method of cleaning a drill sleeve, wherein, the drill sleeve, comprises: an outer sleeve with an internal collet at a distal end of the outer sleeve and an inner opening; a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger wherein the biasing force drives the inner sleeve into the outer sleeve, the method including: rotating the trigger away from the biasing member and handle; sliding the trigger and inner tube out of the inner tube; cleaning the trigger, inner tube, handle, outer tube, and biasing member; sliding the trigger and inner tube into the inner tube; rotating the trigger towards the biasing member and handle so that the biasing member engages the trigger.

Various embodiments are described, wherein the biasing member is a leaf spring attached to the handle, the leaf spring includes an engagement member configured to engage a trigger groove on the trigger, and rotating the trigger away from the biasing member and handle includes disengaging the engagement member from the trigger groove.

Various embodiments are described, wherein rotating the trigger towards the biasing member and handle so that the biasing member engages the trigger includes engaging the engagement member with the trigger groove.

Various embodiments are described, wherein the engagement member is V-shaped.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments may be combined with one or more other embodiments to form new embodiments.

In the majority of cases, surgeons prefer to place screws in a nominal plate hole direction. This helps avoiding screw collisions, ensures the best plate-screw connection strength and is designed to fit most of the patients. However finding the nominal screw direction of an orthopedic plate hole is often challenging. Especially in anatomic plates and holes not perpendicular to plate surface. Testing using threaded sleeves in different kind of threaded holes showed mean deviations of up to 5.65° and worst case of 19.5° vs nominal axis. In some types of plate holes there are no other structures than the thread including chamfers which may be used for orientation and fixation of a drill sleeve.

One way to solve this problem is to use a threaded drill guide. Such a drill guide has a threaded distal end that is threaded into a screw hole in the bone plate, and then the surgeon may drill the screw hole in the precisely correct direction. Screwing the drill guide into the plate hole and then unscrewing the drill guide takes time and effort, increasing the time it takes to secure a plate to a bone. Also as described above, thread drill guides may result in angular variations from the nominal or 0° location. Embodiments of a self-orienting drill sleeve that may be quickly inserted and removed will be described.

Figure 1:
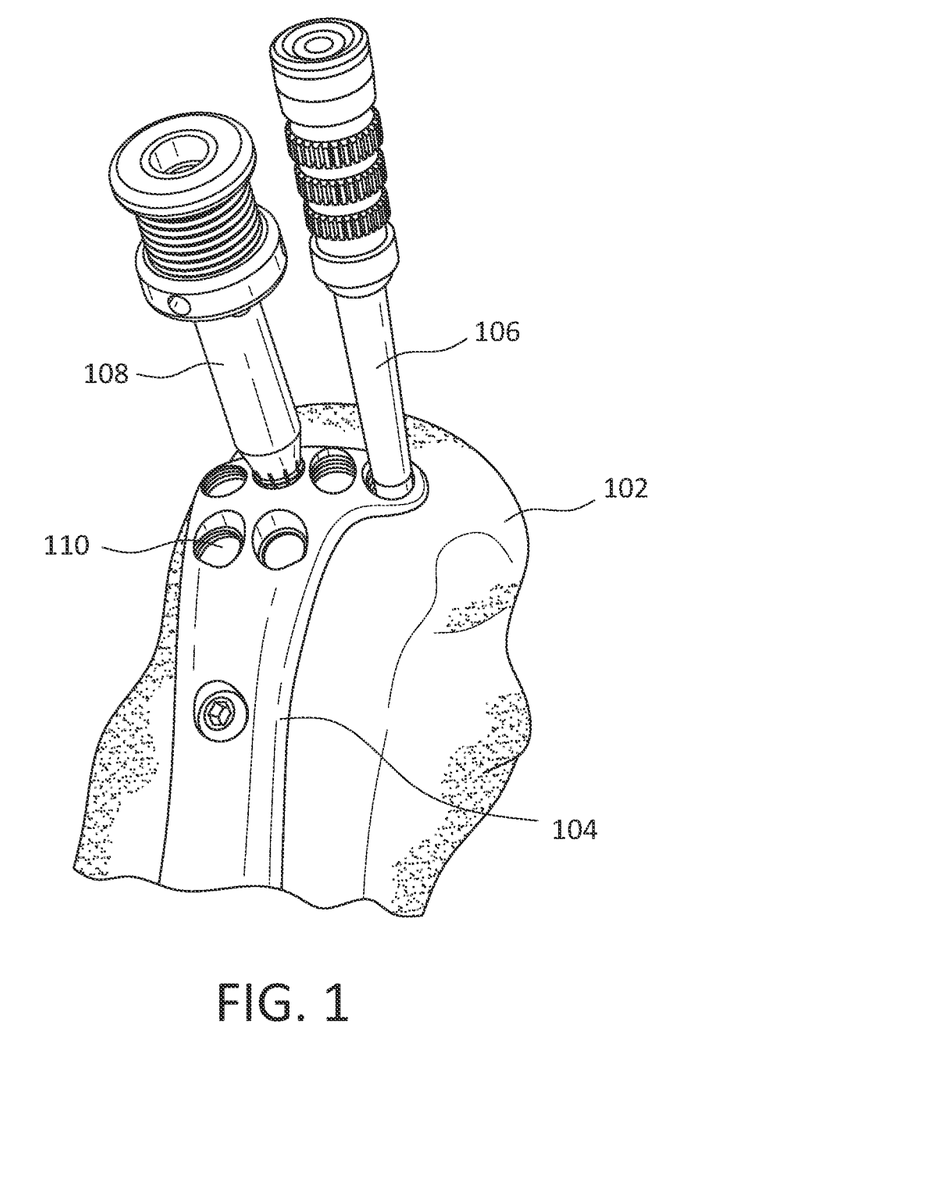
FIG. 1 illustrates an bone plate on a bone.

FIG. 1 illustrates a bone plate 104 on a bone 102. As can be seen the bone plate 104 has a specific shape matching the shape of the bone 102. The bone plate 104 includes a number of different holes 110 with a nominal hole direction. When these nominal hole directions are used, the surgeon can be confident that there will be no screw collisions. However, as discussed above, it is difficult to ascertain the nominal hole directions in plates with complex shapes. A threaded drill guide 106 is shown as screwed into a screw hole 110. The threaded drill guide 106 has a threaded distal end that is screwed into the screw hole 110. It takes time and effort to screw and unscrew the drill guide. Also shown is a second embodiment of a self-orienting drill sleeve 108 inserted into a screw hole 110. This self-orienting drill sleeve 108 has a mechanism and distal end that allows the drill sleeve 108 to be quickly inserted and removed from the plate hole 110 while aligning the drill sleeve 108 with the nominal plate hole direction.

Figure 2:
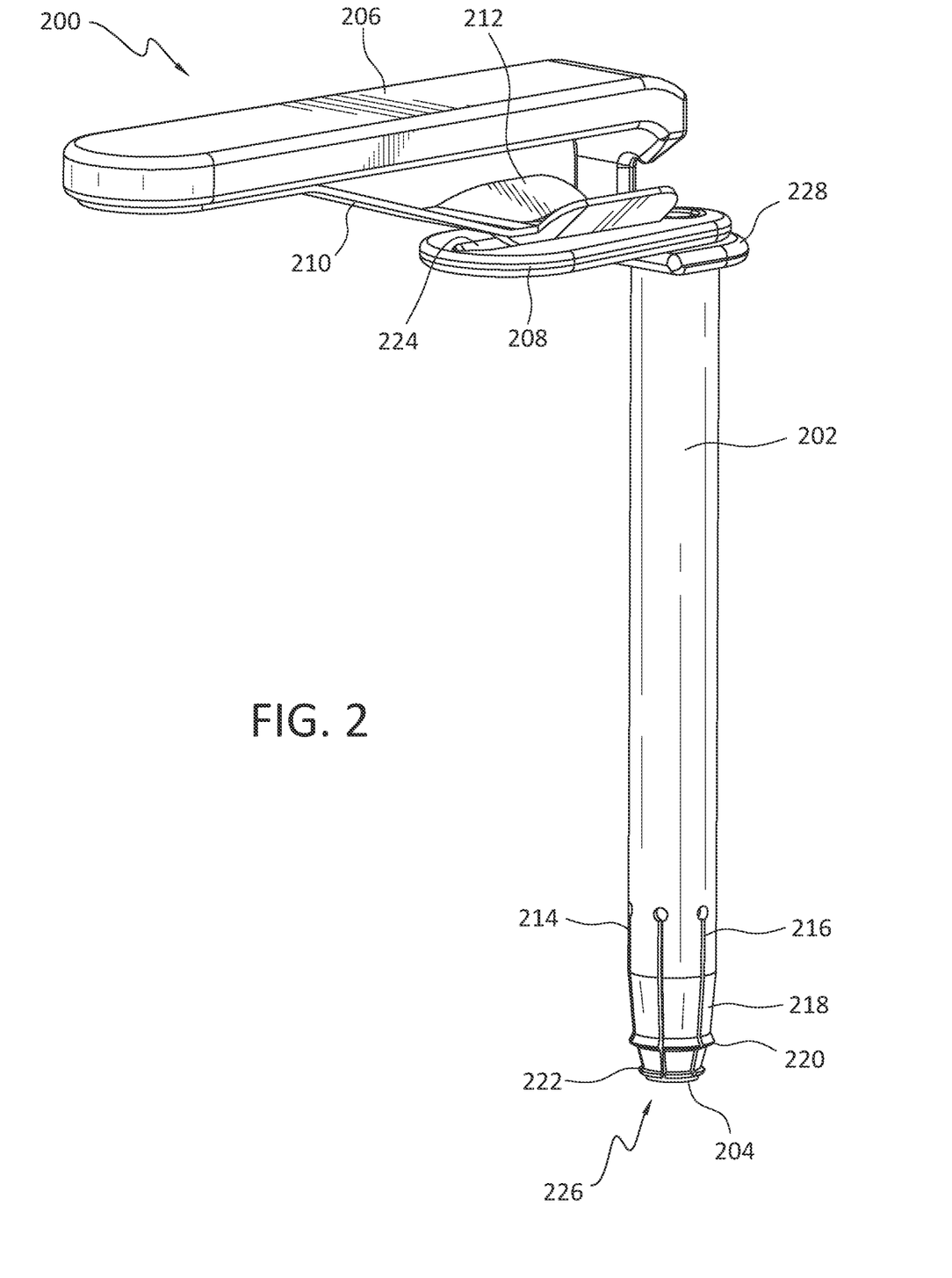
FIG. 2 illustrates a first embodiment of a self-orienting drill sleeve.

FIG. 2 illustrates a first embodiment of a self-orienting drill sleeve 200. The drill sleeve 200 includes an outer sleeve 202 and an inner sleeve 204. The inner sleeve 204 has tubular shape with an opening 230 therethrough (see FIG. 3) that may accept a drill bit. A trigger 208 is attached to a proximal end of the inner sleeve 204. A handle 206 is attached to a proximal end of the outer sleeve 202. A spring 210 is attached to the handle 206. The spring 210 may be a leaf spring that has an engagement member 212 at its end. The engagement member 212 may be V-shaped and is configured to engage a trigger groove 224 on the top of the trigger 208. The spring 210 acts as a biasing member that biases the trigger 208 downward (i.e., the inner sleeve 204 is pushed into the outer sleeve 202 toward their distal ends). While specific shapes are illustrated for the handle 206, trigger 208, and the spring 210, other shapes may be used as well.

Figure 3A:
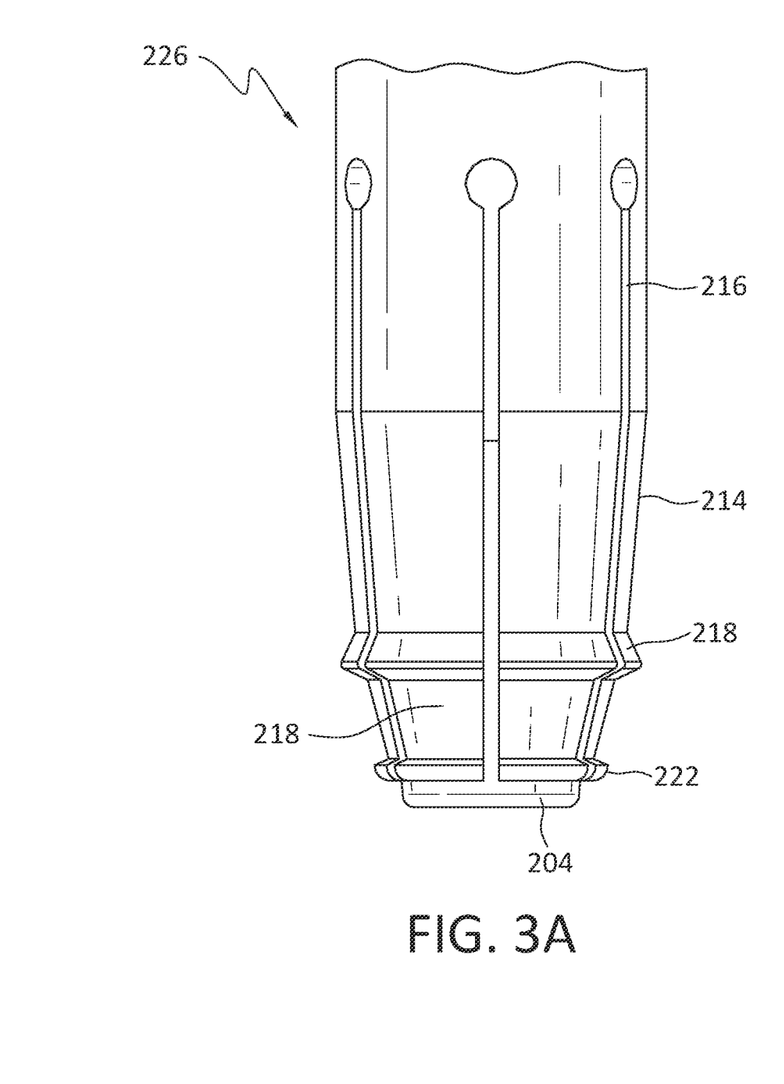
FIGS. 3A and 3B are side and cross-sectional views of a distal end of the drill sleeve in greater detail.
Figure 3B:
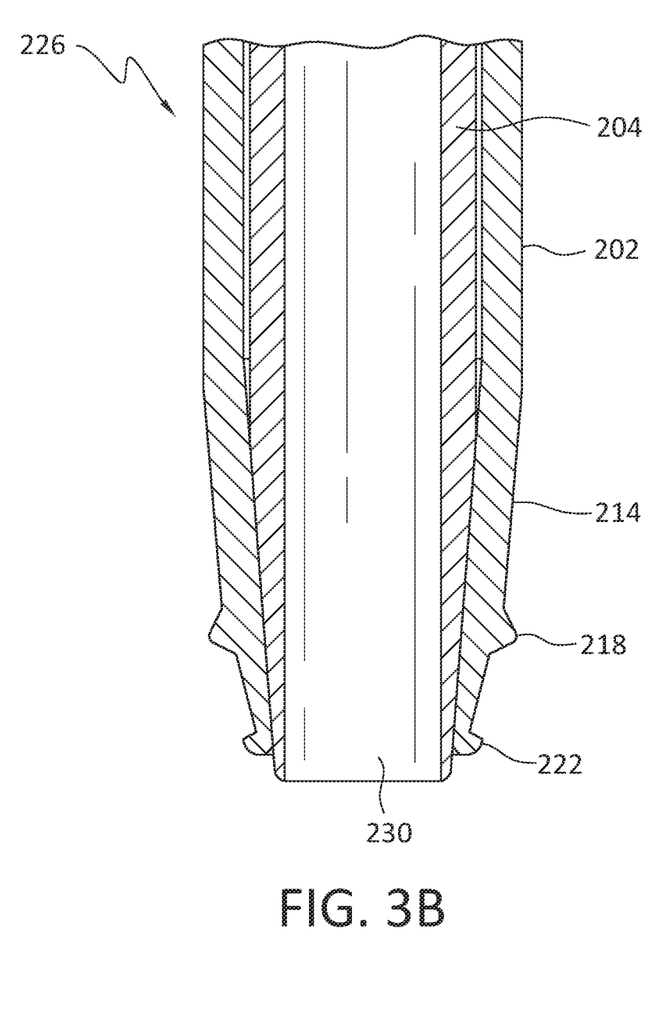

FIGS. 3A and 3B are side and cross-sectional views of a distal end 226 of the drill sleeve 200 in greater detail. The distal end of the outer sleeve 202 includes an internal collet 214. The internal collet 214 is formed by slots 216 in the distal end of the inner sleeve that forms blades 218 between the slots 216. These blades 218 are flexible. The inner collet 214 is sized to fit within the screw hole of a bone plate. When the inner sleeve 204 is inserted inside the internal collet 214, the blades 218 are configured to engage the screw hole of a bone plate. Depending upon the specific sizes of the internal collet 214 and the distal end of the inner tube 204, the blades may be forced outward, when the inner sleeve 204 is inserted in the internal collet. This will be described in more detail below. The internal collet 214 also includes a collet stop 220. The collet stop 220 engages the top of the screw hole to limit insertion of the internal collet 214 into the screw hole. The internal collet 214 further includes a locking ridge 222. The locking ridge 222 is a structure configured to, in conjunction with the stop 220, engage the screw hole so as to lock and orient the drill sleeve 200 in the screw hole. The inner sleeve 204 includes the inner sleeve opening 230 that receives and aligns the drill bit used to drill a hole in the bone.

FIGS. 4A to 4D illustrate a cross-sectional view of the drill sleeve 200 being inserted into the screw hole 252 and being secured to the screw hole 252. FIG. 5A is a cross-sectional view of the distal end of the drill sleeve 200 as it approaches the screw hole 252 corresponding to FIG. 4A. FIG. 5B is a cross-sectional view of the distal end of the drill sleeve 200 after it has been secured to the screw hole 252 corresponding to FIG. 4D.

Figures 4A, 4B:
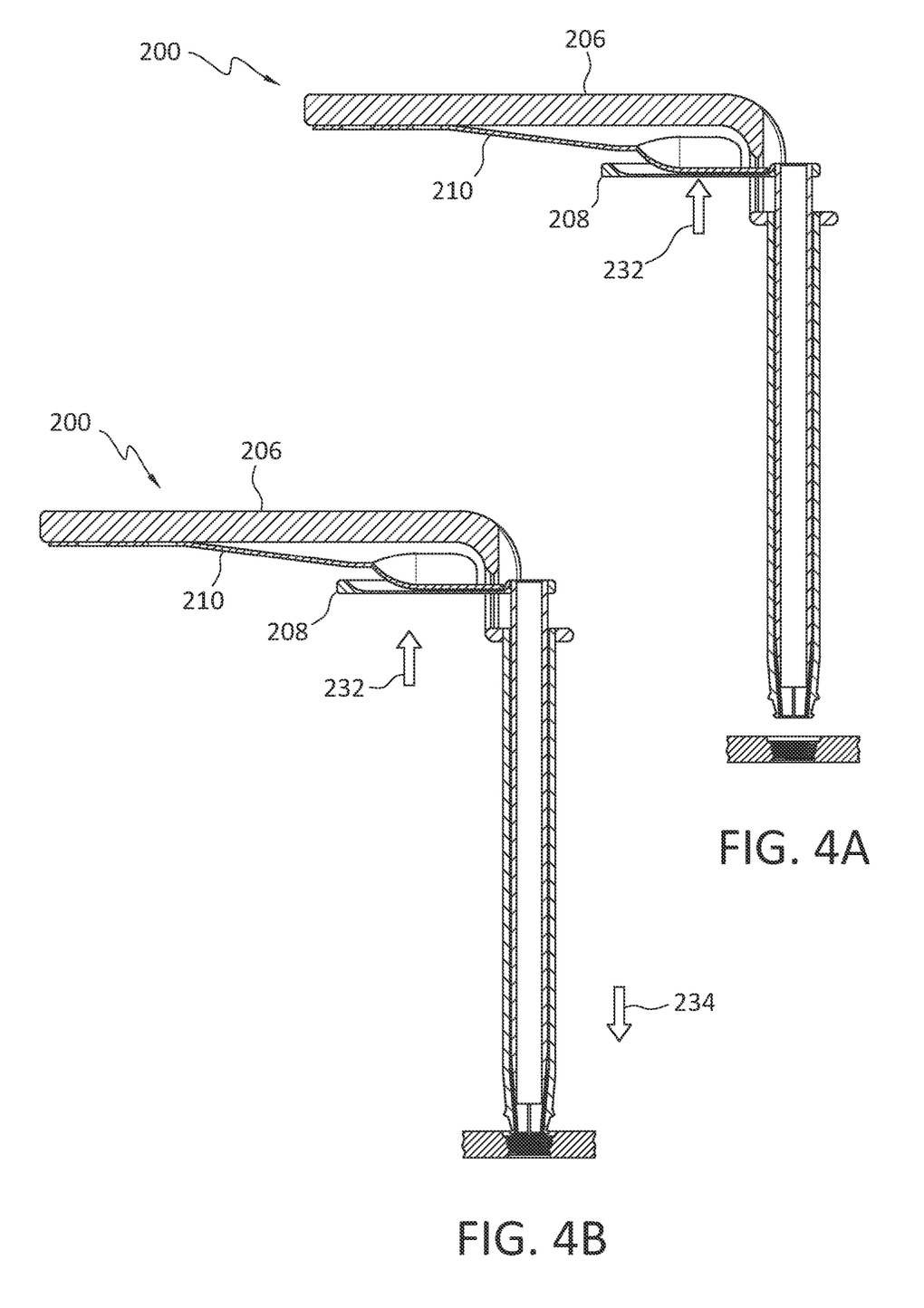
FIGS. 4A to 4D illustrate a cross-sectional view of the drill sleeve being inserted into the screw hole and being secured to the screw hole.
Figures 4C, 4D:
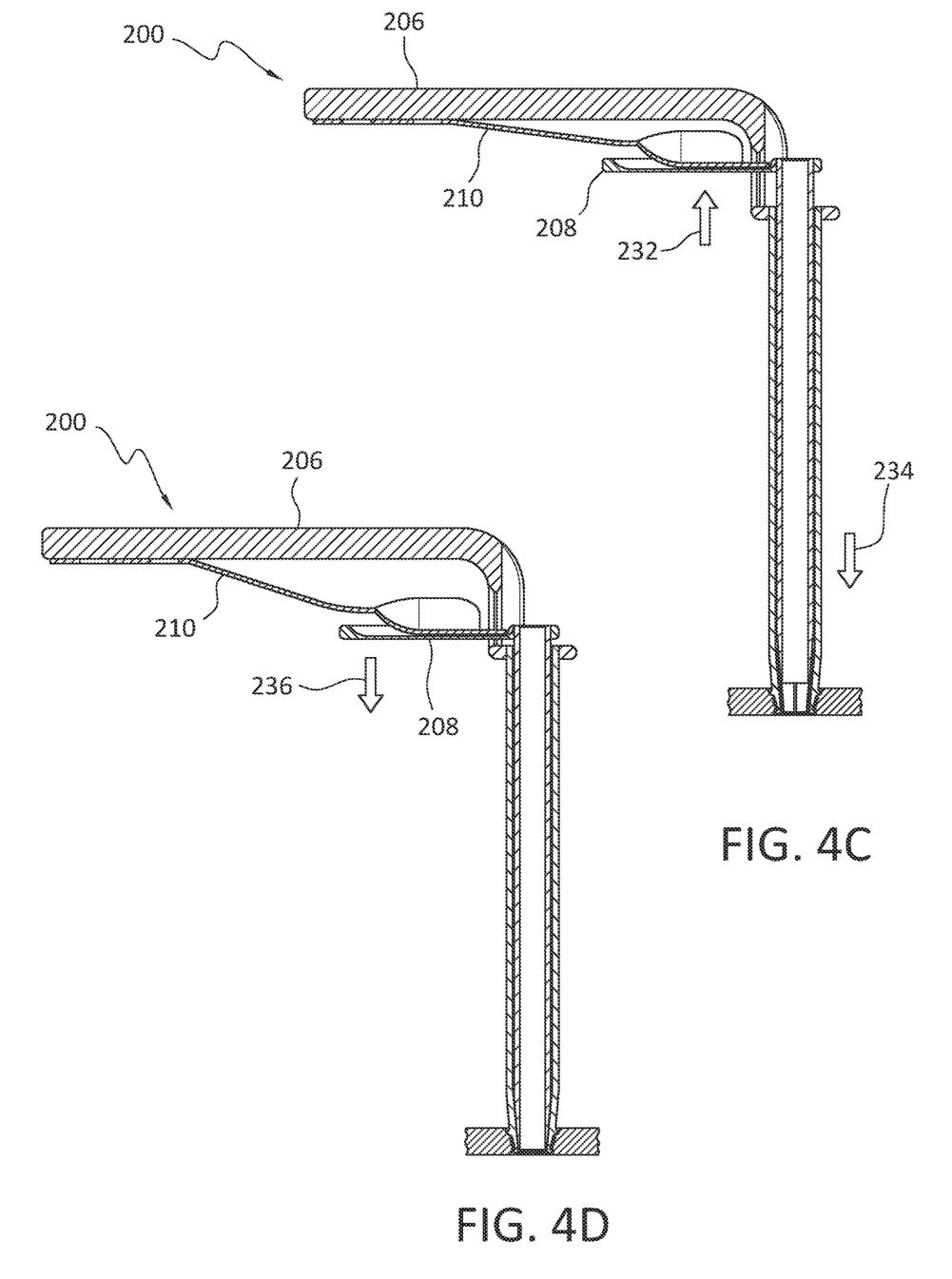
Figure 5A:
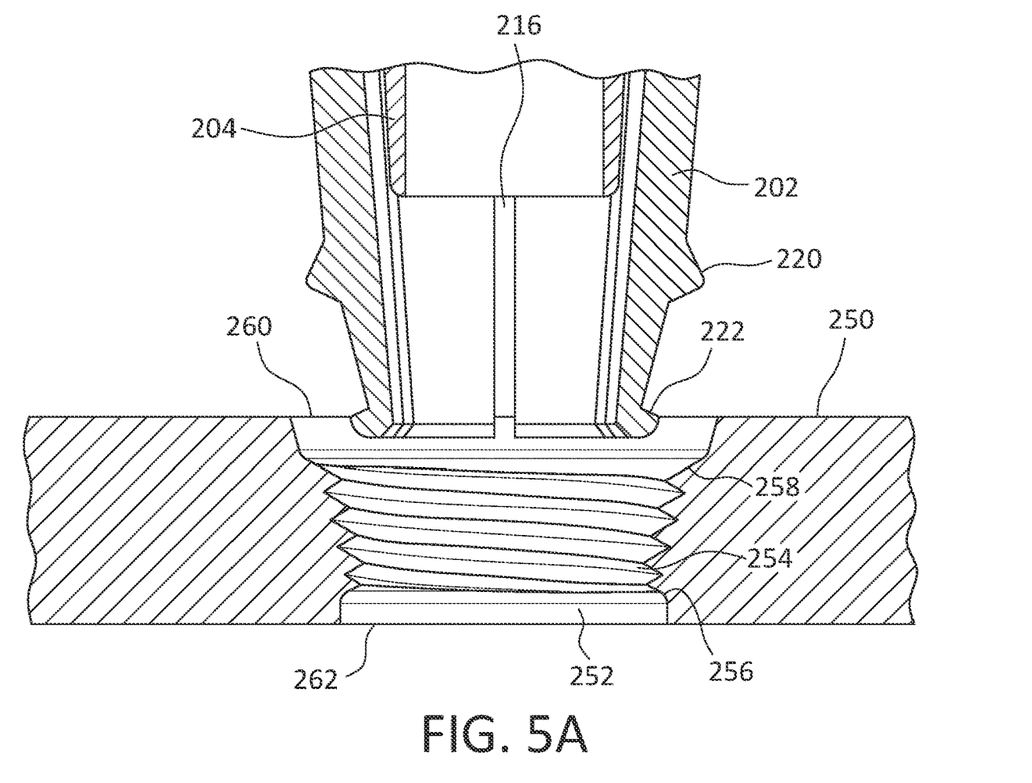
FIG. 5A is a cross-sectional view of the distal end of the drill sleeve as it approaches the screw hole corresponding to FIG. 4A.
Figure 5B:
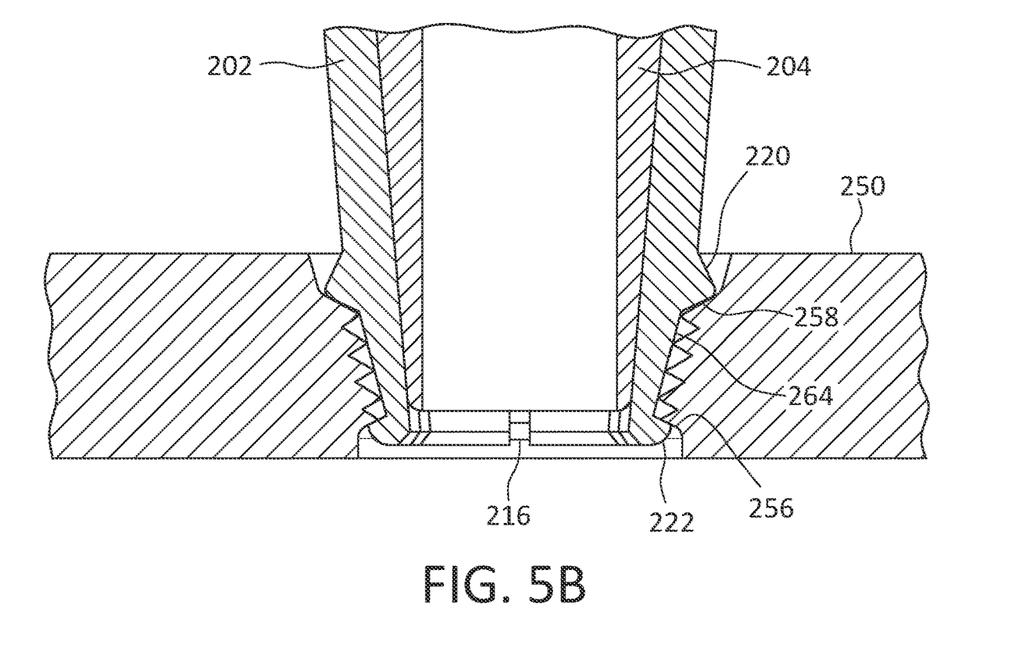
FIG. 5B is a cross-sectional view of the distal end of the drill sleeve after it has been secured to the screw hole corresponding to FIG. 4D.

In FIG. 4A the surgeon grips the handle 206 and squeezes the trigger 208 and applies a force 232 upward against the spring 210. Squeezing the trigger 206 withdraws the inner sleeve 204 upward from the outer sleeve 204. More specifically, the distal end of the inner sleeve 204 is withdrawn from the inner collet 214, which allows the blades 218 to bend inward as the blades 218 are flexible. In FIG. 4B, the drill sleeve 200 is moved 234 towards the screw hole 252 and begins to enter the screw hole 252 when the distal end 226 passes through a first opening 260 of the screw hole 252. As the drill sleeve 200 continues to move 234 towards the screw hole 252, the distal end 226 of the drill guide 200 becomes seated in the screw hole 252 as shown in FIG. 4C. This occurs when, as illustrated in FIG. 5B, the stop 220 comes into contact with a seat 258 in the screw hole 252. The seat 258 may be a top edge of the threads 254 of the screw hole 252. When the stop 220 contacts the seat 258, the movement 234 of the drill sleeve 200 is impeded. Further, as the distal end 226 moves into the screw hole 252, the locking ridge 220 may come into contact with some of the threads 254, which causes the blades 218 to bend inward as the distal end 226 progresses into the screw hole 252. Once the stop 220 engages the seat 258, the locking ridge 222 has passed through the threads 254 and now springs back to engage the locking edge 256 of the screw hole as the blade 218 returns to its normal position. At this point, with the stop 220 engaging the seat 258 and the locking edge 222 engaging the locking edge 256, the distal end 226 of the drill sleeve 200 is loosely secured and aligned in the screw hole 252. At this moment, the drill sleeve has a tendency to align itself with the nominal axis of the plate hole, due to the spring blades 18 wanting to return to nominal position.

In FIG. 4D, the surgeon releases 236 the trigger 208, and the spring 210 biases the inner tube 204 downward towards the distal end 226 of the drill sleeve 200. A distal end of the inner tube 204 comes into contact with the blades 218, this prevents the blades from moving inward. Thus, the locking ridge 222 is forced into engagement with the locking edge 256 to secure the drill sleeve 200. Also, the blades 218 are unable to bend inward so that the locking ridge 222 is held in contact with the locking edge 256. The angles of the seat 258 and the locking ridge 256 may be chosen so that as the inner tube 204 pushes against the blades 218, the blades 218 via the stop 220 and locking edge 222 are held more securely against the locking edge 258 and the seat 258. This may be accomplished when the angle between the edges of the stop 220 and locking edge 222 are greater than or increase relative to the angle between edges on the stop 220 and the locking ridge 222.

The distal end 226 and blades 218 include an interim surface 264 the extends between the stop 220 and the locking ridge 222. In some embodiments, this interim edge may also engage the threads 254, which engagement may further secure and align the drill sleeve 200 in the screw hole 252.

Once the drill sleeve 200 has been secured to the screw hole 252, the surgeon may then drill a hole into the underlying bone. Next, the surgeon may quickly remove the drill sleeve 200 by depressing the trigger 208 and removing the distal end 226 of the drill sleeve 200 from the screw hole 252. As a result, a surgeon may quickly insert the drill sleeve 200 into a screw hole 252, drill the hole, and then quickly remove the drill sleeve 200 from the screw hole 252. This will save a surgeon a significant amount of time and effort versus threading and unthreading a threaded drill guide from the screw hole.

In the embodiment described above, the outer diameter of the distal end of the inner sleeve 204 and the inner diameter of the internal collet 214 are sized to be substantially the same size and are substantially cylindrical. Other geometries may be used as well.

For example, the inner diameter of the internal collet 214 may be tapered. In such a situation the inner sleeve will push the blades 218 outward as the distal end of the inner sleeve 204 is advanced into the internal collet 214 so as to have the blades 218 engage the screw hole 252 as described above. The diameter of internal collet 214 at the locking ridge 222 may be sized to be larger or smaller than the smallest diameter of the screw hole 252, as the screw hole may have a frustoconical shape. If the diameter of the locking ridges 222 is larger, then the locking ridges 222 may contact the threads 254 as the distal end 226 of the drill sleeve enters the screw hole 252. This will cause the blades 218 to bend inward to allow the distal end 226 to progress into the screw hole 252. Once the stop 222 reaches the seat 258, the locking ridge 222 will be clear of the threads 254, and the blades 218 will expand outward allowing the ridge 222 to contact the locking edge 256.

If the diameter of the locking ridge 222 is smaller than the smallest diameter of the screw hole, the distal end 226 of the drill sleeve 200 may freely enter the screw hole 252 with out the blades 218 needing to bend inward. Then when the distal end of the inner tube 204 enters the internal collet, the blades 218 are pushed outward so that the ridge 222 contacts and engages the locking ridge 256. Further, in this embodiment, the distal end of the inner tube 204 may be substantially cylindrical or tapered.

Various geometric parameters of the drill sleeve 200 affect how the drill sleeve 200 is secured to a screw hole 252. For example, the length of the inner tube versus the outer tube 202 affects how far the distal end of the inner tube 202 enters into the internal collet 214 at the end of the outer tube 202. This affects how much force the inner tube 202 applies against the blades 202 and hence helps to secure the drill sleeve 200 to the screw hole 252. Further, the shapes of the distal end of the inner tube 204 and the internal diameter of the internal collet 214 may be selected to be cylindrical or tapered. It has to be noted that the taper angle influences the force exerted on the internal collet 214, and this angle will be selected in combination with the spring force of the spring 210. Also, the sizes of the distal end of the inner tube 204 and the internal diameter of the internal collet 214 may be selected to be substantially the same or slightly different to allow distal end of the inner tube 204 to apply force to the blades 218.

Also, the size, location, and shape of the stop 220, locking ridge 222, locking ridge 256, and seat 258 are selected to complement one another and to facilitate a secure and self-orienting connection of the drill sleeve 200 to the screw hole 252.

Figures 6A, 6B, 6C:
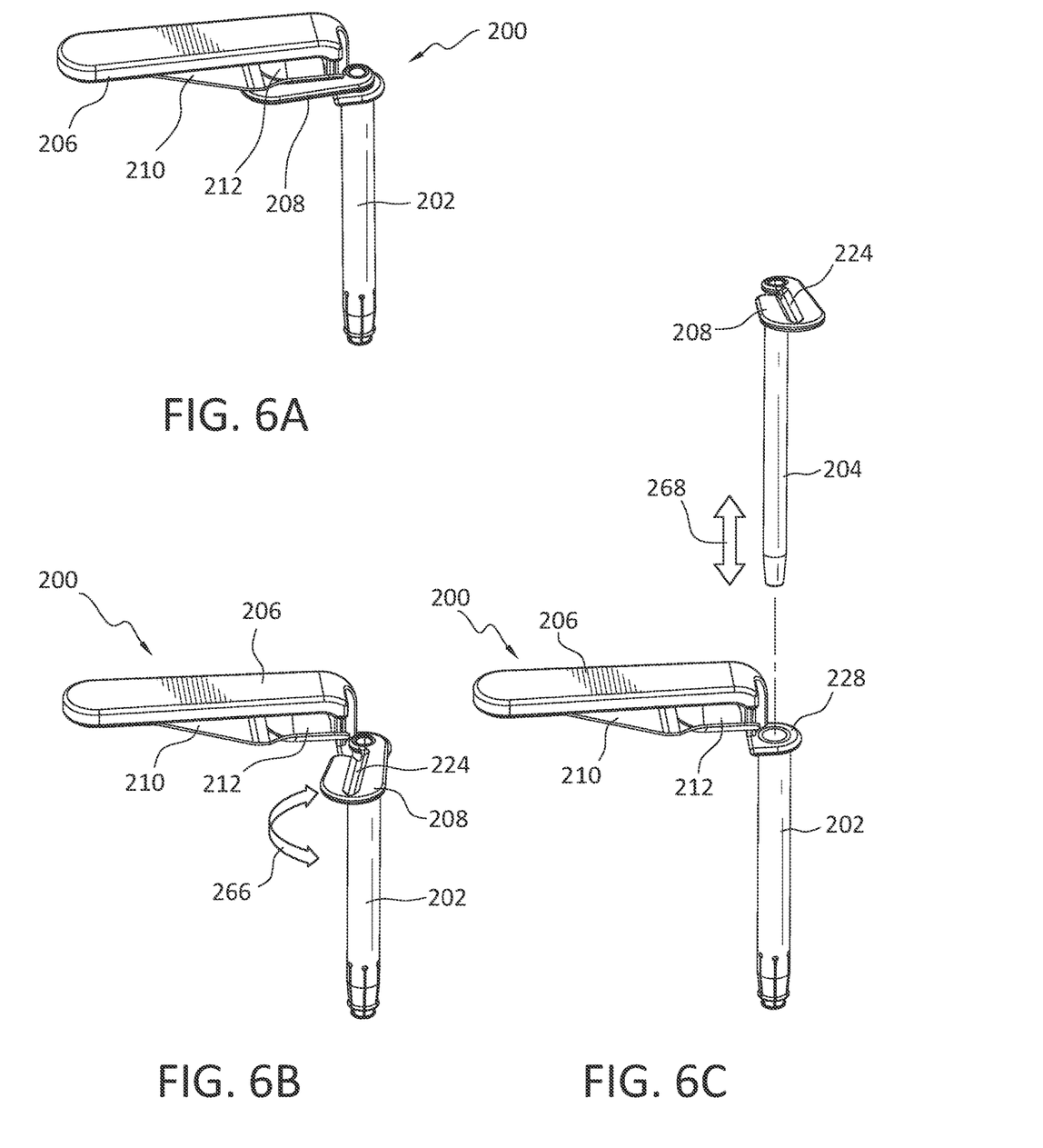
FIGS. 6A to 6C illustrate how the drill sleeve may be disassembled for cleaning.

The drill guide 200 of FIG. 2 also has the benefit of being able to be easily disassembled to allow the drill guide to be easily cleaned and sanitized for reuse. FIGS. 6A to 6C illustrate how the drill sleeve 200 may be disassembled for cleaning. FIG. 6A illustrates a perspective view of the drill sleeve 200 in its normal configuration. FIG. 6B illustrates a first step in disassembling the drill sleeve 200. The trigger 208 is rotated and disengaged from the engagement member 212 of the spring 210. Once the trigger 208 is rotated free of the engagement member 212 and the handle 206, the trigger 208 and inner tube 204 assembly is lifted out 268 from the outer tube 202 as illustrated in FIG. 6C. With the inner tube 204 separated from the outer tube 202, the parts of the drill sleeve 200 may now be effectively cleaned and sanitized. The drill sleeve 200 may be reassembled in the opposite order. The inner tube 204 is inserted 268 into the outer tube 202 and slid until the trigger 208 engages the sleeve stop 228. Then the trigger 208 is rotated back towards 266 the engagement member 212 of the spring 210. The trigger 208 slides under the engagement member 212 until the engagement member 212 engages a trigger groove 224 to prevent further rotation of the trigger 208. At this point, the drill sleeve 200 has been reassembled and is ready for use.

Figure 7A:
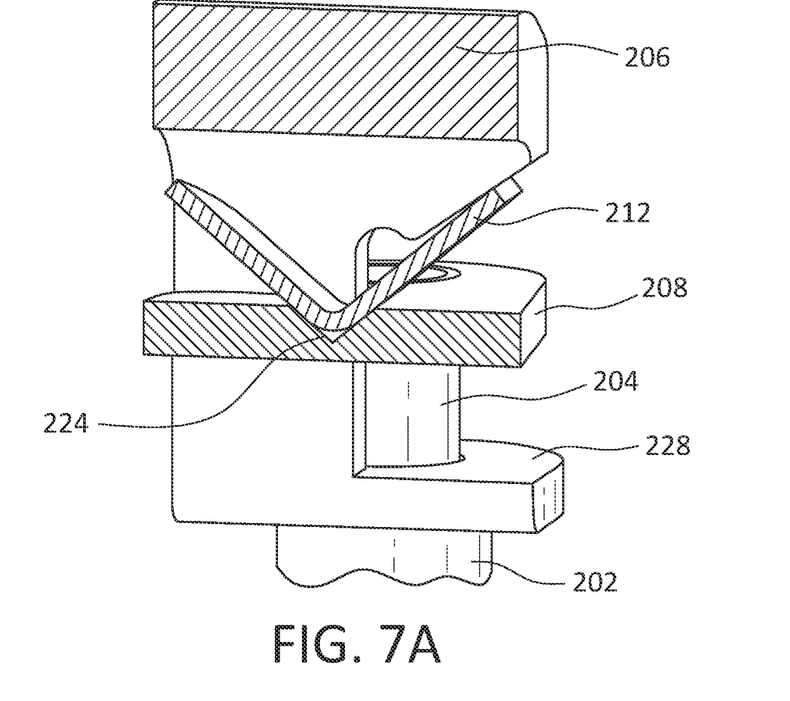
FIGS. 7A and 7B are cross-sectional views of the trigger, engagement member, and the handle that illustrate the interaction between the engagement member and the trigger groove.
Figure 7B:
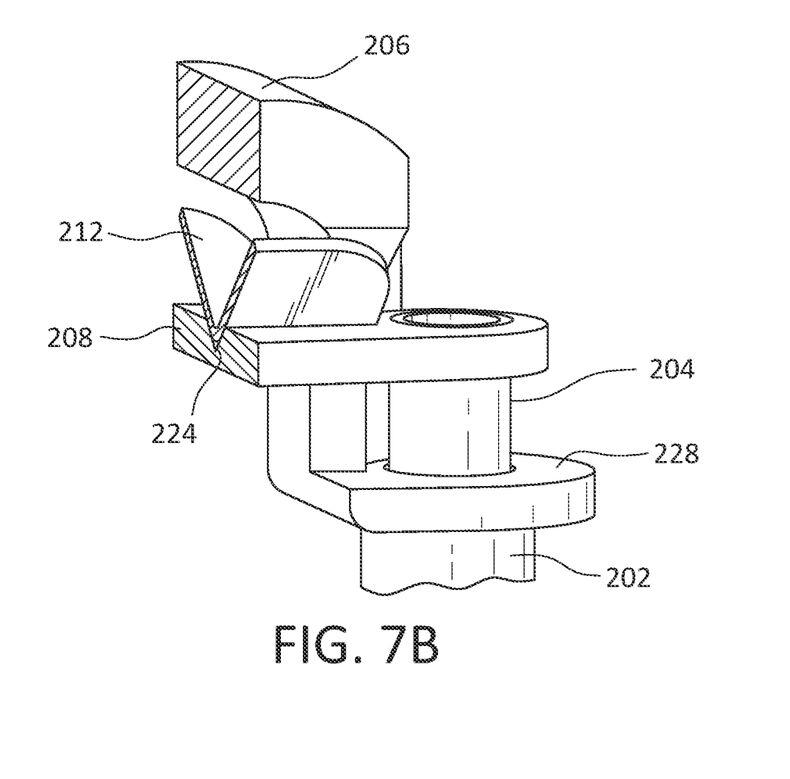

FIGS. 7A and 7B are cross-sectional views of the trigger 208, engagement member 212, and the handle 206 that illustrate the interaction between the engagement member 212 and the trigger groove 224. The engagement member 212 is shown as being V-shaped. The bottom of the V-shaped engagement member 212 engages the trigger groove 224 and applies a biasing force downward on the trigger 208. The trigger groove 224 may be V-shaped as well corresponding the V-shape of the engagement member 212. The engagement member 212 keeps the trigger 208 generally aligned with the handle 206. As described above, the surgeon may squeeze the trigger 208 towards the handle 206. The spring 210 is designed to apply sufficient force to bias the distal end of the inner tube 204 into the internal collet 214. Further, the bias force is sufficient to engage the trigger groove 224 to prevent unwanted rotation of the trigger 208 relative to the handle 206. Further, the spring 210 is designed to allow a surgeon to squeeze the trigger 208 by hand to draw the inner tube 204 upward while engaging and disengaging the drill sleeve 200 from the screw hole 252. Also, the spring 210 is designed so that the bias force is small enough so that the trigger 208 may be reasonably rotated away from the engagement member 212 for disassembly of the drill sleeve. The V-shape of the engagement member 212 also facilitates easy rotation of the trigger 208 back into is assembled position, as the trigger will engage the side of the V and then as the trigger is rotated, the V-shaped engagement member will rise until the bottom of the V aligns with the trigger groove 224 and engages the trigger groove 224.

While the engagement member 212 and the trigger groove 224 are illustrated as V-shaped, other complementary shapes may be used as well, including shapes that include curved and/or straight sides.

Figure 8A:
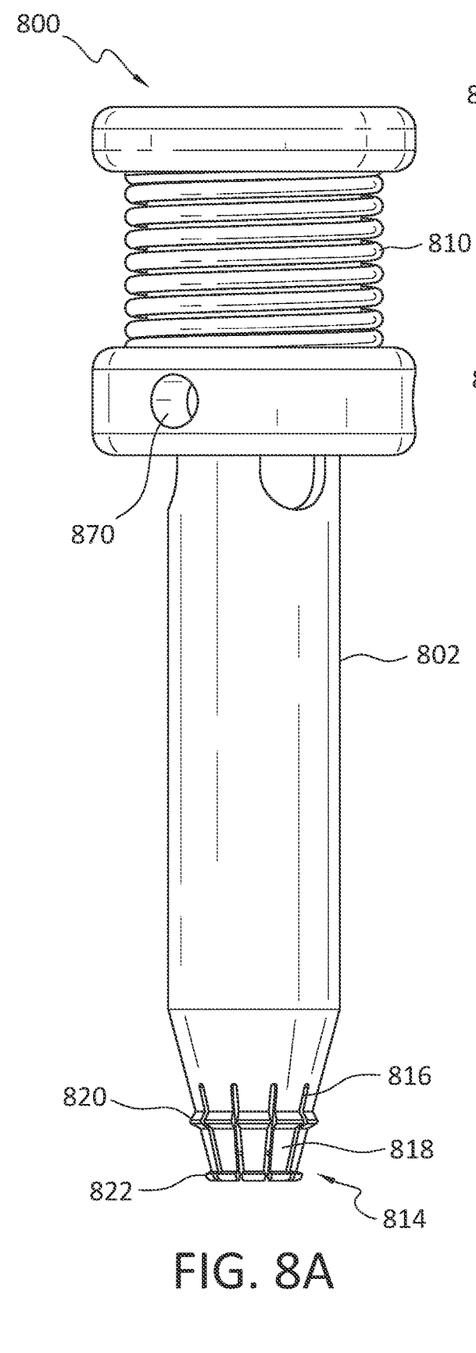
FIGS. 8A, 8B, and 8C illustrate side, cross-sectional, and perspective exploded views of a second embodiment of a drill sleeve.
Figure 8B:
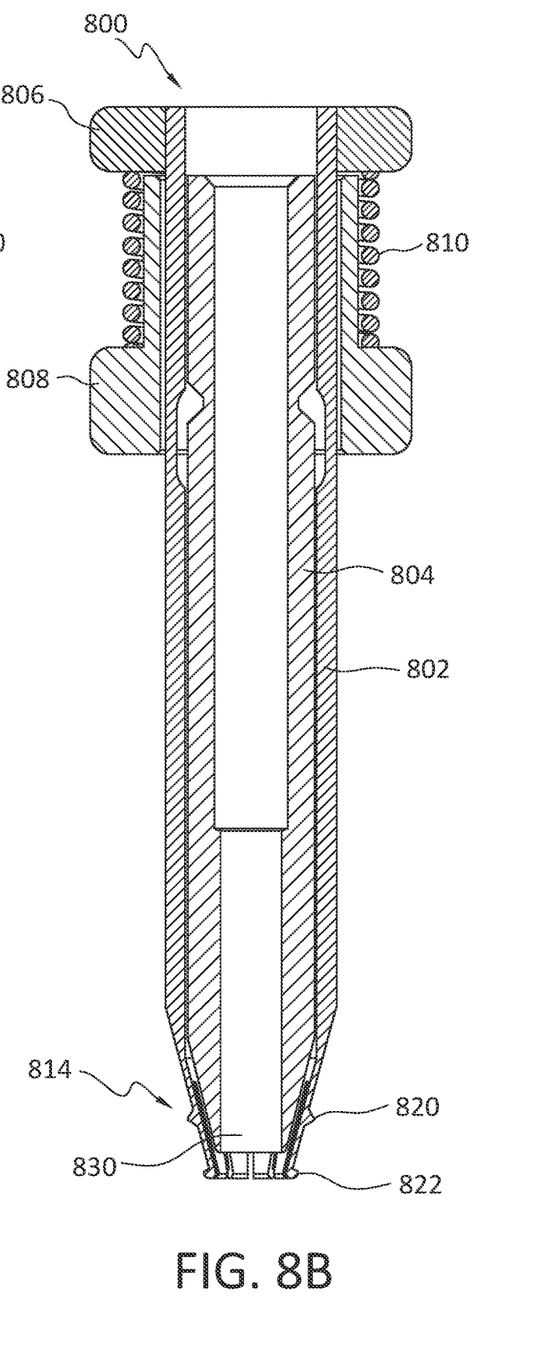
Figure 8C:
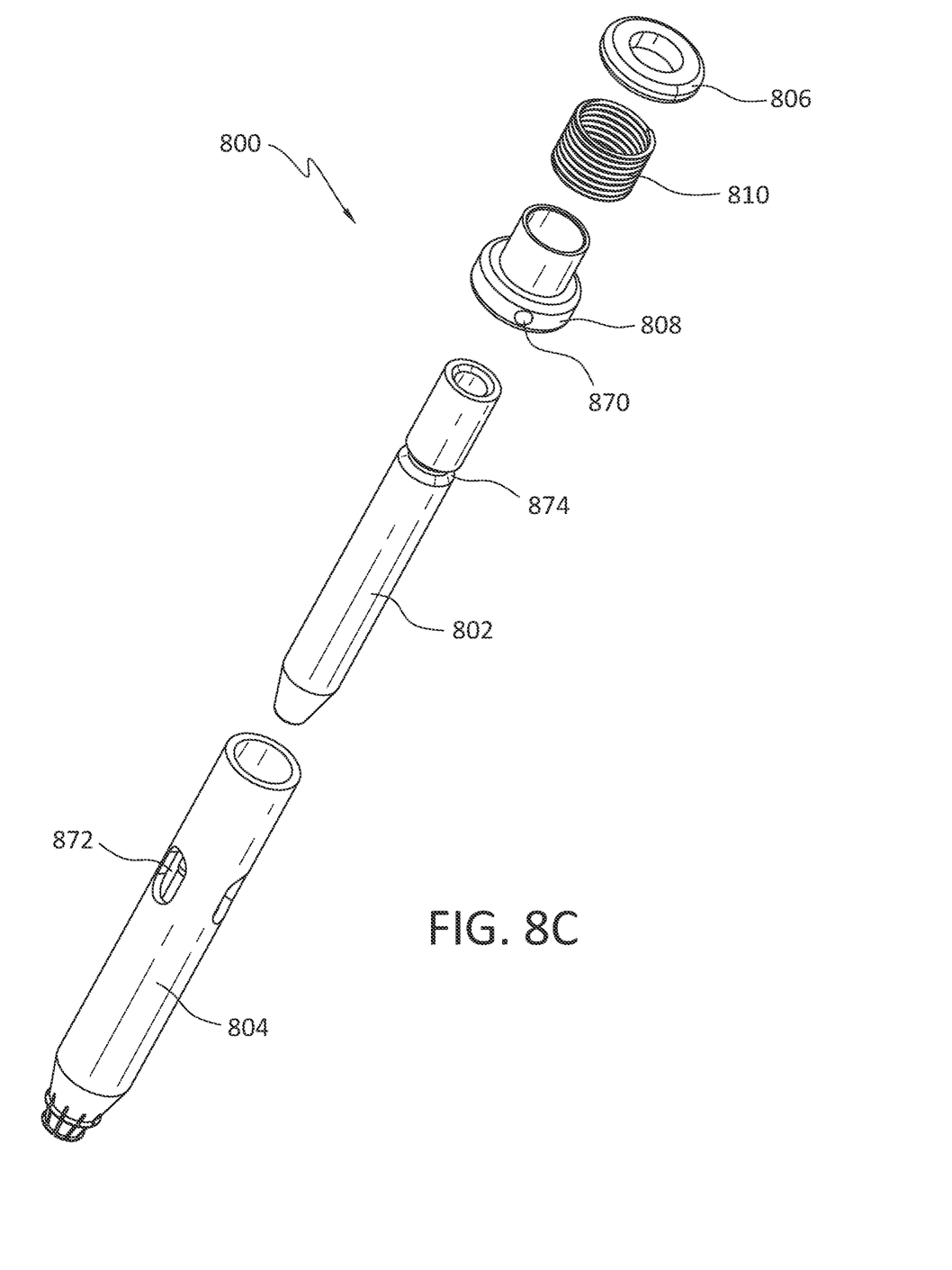

FIGS. 8A, 8B, and 8C illustrate side, cross-sectional, and perspective exploded views of a second embodiment of a drill sleeve 800. The drill sleeve 800 has an inner tube 802 and an outer tube 804 like the first drill sleeve 200. Further the distal end of the outer tube 804 has an internal collet 814 similar to the first drill sleeve 200. It is noted that the distal end of the inner tube 804 has a tapered end that engages the blades 818 of the internal collet 814.

The drill sleeve 800 includes a handle 806 that is attached to the outer tube 802. The drill sleeve 800 also has a trigger 808. The trigger 808 is attached to the inner tube 802 using a connection member such as a pin (not shown) inserted into a trigger hole 870 that extends through a slot 872 in the outer tube 804 and engages an inner tube groove 874. More than one trigger hole 870 and pin may be used as well. As a result, when the trigger 808 moves up and down, the inner tube 804 moves up and down along with the trigger 808. Other connection schemes may be used to connect the trigger 808 to the inner tube 804.

The drill sleeve 800 operates in a similar manner to that as drill sleeve 200. FIGS. 9A to 9D illustrate a cross-sectional view of the drill sleeve 800 being inserted into the screw hole 852 and being secured to the screw hole 852.

Figure 9A:
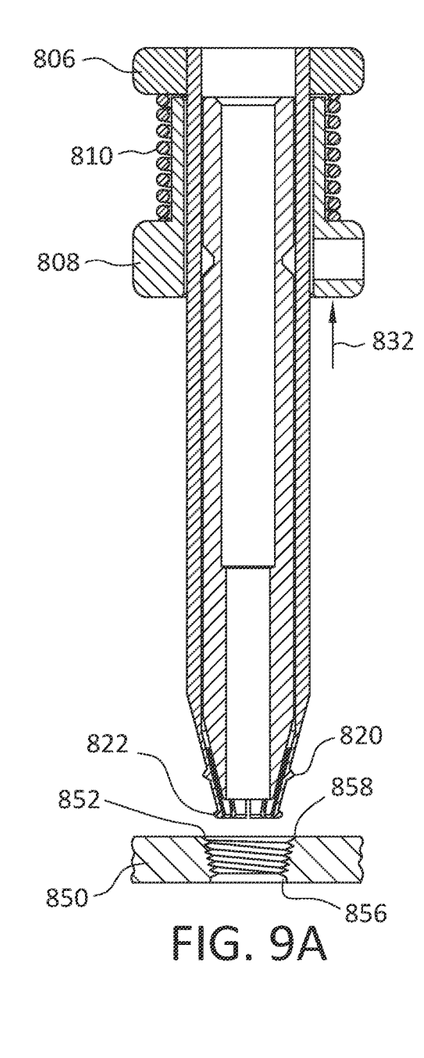
FIGS. 9A to 9D illustrate a cross-sectional view of the drill sleeve being inserted into the screw hole and being secured to the screw hole.
Figure 9B:
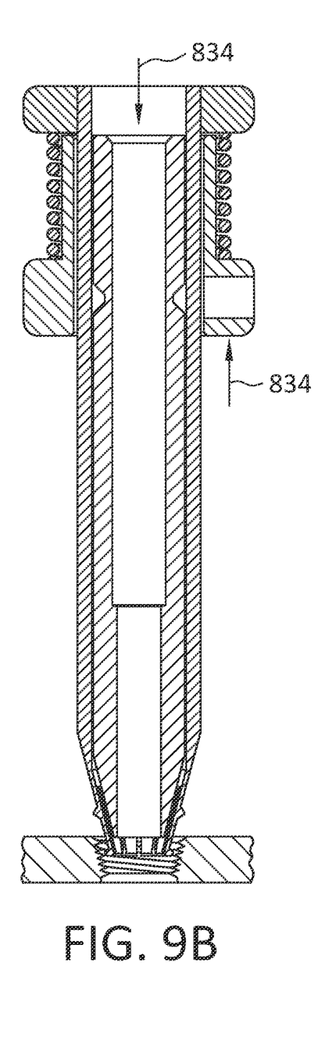
Figure 9C:
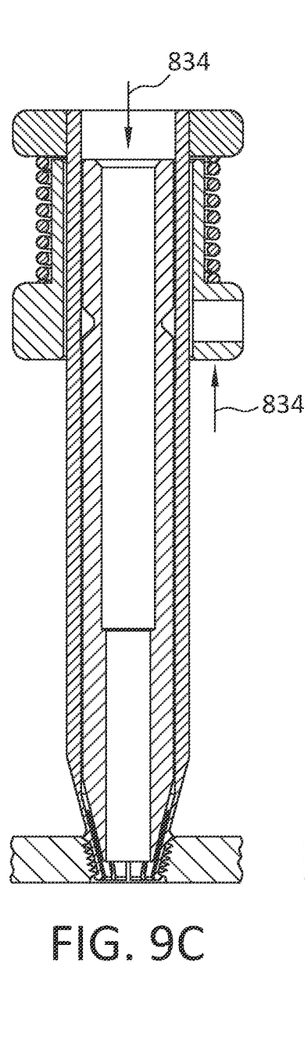
Figure 9D:
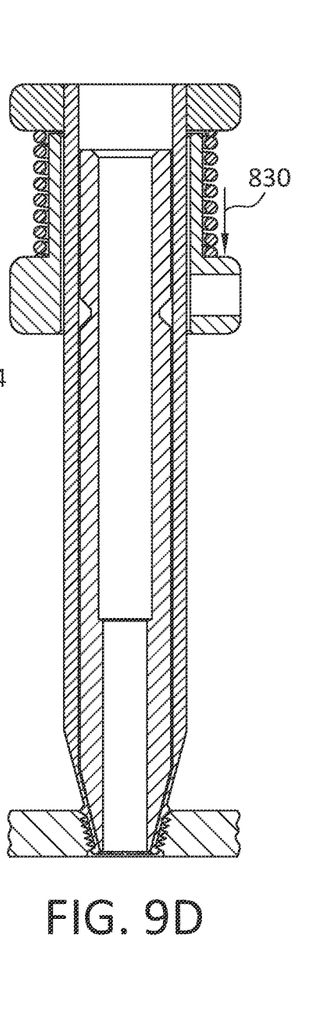

In FIG. 9A the surgeon grips the handle 806 and squeezes the trigger 808 and applies a force 832 upward against the spring 810 and withdraws the inner sleeve 804 upward from the outer sleeve 802. More specifically, the distal end of the inner sleeve 804 is withdrawn from the inner collet 814, which allows the blades 818 to bend inward. In FIG. 9B, the drill sleeve 800 is moved 834 towards the screw hole 852 and begins to enter the screw hole 852. The internal collet 814 engages the screw hole 852 as shown in FIGS. 9C and 9D in the same manner as described above with respect to FIGS. 4A to 4D, 5A, and 5B. To remove the drill sleeve 800, the surgeon again depresses the trigger 808 and removes the drill sleeve 800 from the screw hole 852.

The spring 810 is shown as a coil spring but other types of cylindrical springs may be used. Further, the spring 810 is designed to apply sufficient biasing force to drive the inner tube 202 downward into the outer tube 802. Further, the biasing force generated by the spring will be small enough to allow the surgeon to comfortably squeeze the trigger 808 by hand.

The drill sleeve described herein allows a surgeon to quickly insert and remove the drill sleeve from a bone plate screw hole. The drill guide has a structure and mechanism that locks the drill sleeve to the screw hole so as to align the drill guide with the nominal screw hole direction. This allows the surgeon to quickly and confidently insert the drill guide into the screw hole so that it is aligned with the nominal direction of the screw hole, drill a hole into the bone, and then quickly remove the drill sleeve. This is may be done more quickly than with a threaded drill guide.

While each of the embodiments are described above in terms of their structural arrangements, it should be appreciated that the invention also covers the associated methods of using the embodiments described above.

While the techniques described herein may be implemented and have been described in connection with the various embodiments of the various figures, it is to be understood that other similar embodiments may be used or modifications and additions may be made to the described embodiments without deviating therefrom. For example, it should be appreciated that the steps disclosed above may be performed in the order set forth above, or in any other order as desired. Further, one skilled in the art will recognize that the techniques described in the present application may apply to any environment. Therefore, the techniques described herein should not be limited to any single embodiment, but rather should be construed in breadth and scope in accordance with the appended claims.

What is claimed is:

1. A drill sleeve, comprising:
an outer sleeve with an internal collet at a distal end of the outer sleeve and an inner opening;
a handle connected to the outer sleeve;
an inner sleeve with an inner opening configured to receive and guide a drill bit, wherein the inner sleeve is configured to slide inside the inner opening of the outer sleeve;
a trigger connected to the inner sleeve; and
a biasing member configured to apply a biasing force between the handle and the trigger wherein the biasing force drives the inner sleeve into the outer sleeve,
wherein when a distal end of the inner sleeve engages the internal collet, the internal collet is configured to engage a screw hole in a bone plate, align the drill sleeve with a nominal axis of the screw hole, and secure the drill sleeve to the screw hole.

2. The drill sleeve of claim 1, wherein the internal collet includes a plurality of blades configured engage the screw hole.

3. The drill sleeve of claim 2, wherein the internal collet further includes a stop and a locking ridge.

4. The drill sleeve of claim 3, wherein the stop is configured to engage a seat in the screw hole and the locking ridge is configured to engage a locking edge in the screw hole.

5. The drill sleeve of claim 3, wherein a diameter of the internal collet at the locking ridge is less than a smallest diameter of the screw hole.

6. The drill sleeve of claim 1, wherein the biasing member is a leaf spring attached to the handle, wherein the leaf spring includes an engagement member configured to engage a trigger groove on the trigger.

7. The drill sleeve of claim 6, wherein the engagement member is V-shaped.

8. The drill sleeve of claim 1, wherein the distal end if the inner sleeve is substantially cylindrical.

9. The drill sleeve of claim 1, wherein the distal end of the inner sleeve is tapered.

10. The drill sleeve of claim 1, wherein an inner opening of the internal collet is substantially cylindrical.

11. The drill sleeve of claim 1, wherein the inner opening of the internal collet is tapered.

12. The drill sleeve of claim 1, wherein the biasing member is a coil spring surrounding the outer tube and located between the handle and the trigger.

13. The drill sleeve of claim 1, further including a connection member connected to trigger and the inner tube, wherein the connection member passes through a slot in the outer sleeve.

14. The drill sleeve of claim 1, wherein the connection member is a pin that engages a hole in the trigger and a groove in the inner tube.

15. A method of drilling a hole in a bone for a bone plate using a drill sleeve, wherein,
the drill sleeve, comprises: an outer sleeve with an internal collet at a distal end of the outer sleeve and an inner opening; a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger, wherein the biasing force drives the inner sleeve into the outer sleeve, the method comprising:
depressing the trigger of the drill sleeve;
inserting the distal end of the outer sleeve into a screw hole of the bone plate;
releasing the trigger of the drill sleeve to securely engage the screw hole;
drilling a hole in the bone through the screw hole using the drill sleeve;
depressing the trigger; and
removing the distal end of the outer sleeve from the screw hole.

16. The method of claim 15, wherein securely engaging the screw hole includes aligning the drill sleeve with a nominal direction of the screw hole.

17. A method of cleaning a drill sleeve, wherein,
the drill sleeve, comprises: an outer sleeve with an internal collet at a distal end of the outer sleeve and an inner opening; a handle connected to the outer sleeve; an inner sleeve with an inner opening configured to receive and guide a drill bit, wherein the inner sleeve is configured to slide inside the inner opening of the outer sleeve; a trigger connected to the inner sleeve; and a biasing member configured to apply a biasing force between the handle and the trigger, wherein the biasing force drives the inner sleeve into the outer sleeve, the method comprising:
rotating the trigger away from the biasing member and handle;
sliding the trigger and inner sleeve out of the outer sleeve;
cleaning the trigger, inner sleeve, handle, outer sleeve, and biasing member;
sliding the trigger and inner sleeve into the outer sleeve;
rotating the trigger towards the biasing member and handle so that the biasing member engages the trigger.

18. The method of claim 17, wherein
the biasing member is a leaf spring attached to the handle,
the leaf spring includes an engagement member configured to engage a trigger groove on the trigger, and
rotating the trigger away from the biasing member and handle includes disengaging the engagement member from the trigger groove.

19. The method of claim 18, wherein
rotating the trigger towards the biasing member and handle so that the biasing member engages the trigger includes engaging the engagement member with the trigger groove.

20. The method of claim 19, wherein the engagement member is V-shaped.

* * * * *